United States Patent [19]

Kleinstück et al.

[11] Patent Number: 4,931,586
[45] Date of Patent: Jun. 5, 1990

[54] PROCESS FOR THE CONTINUOUS PRODUCTION OF 2-PHOSPHONE-BUTANE-1,2,4-TRICARBOXYLIC ACID AND ALKALI METAL SALTS THEREOF

[75] Inventors: Roland Kleinstück, Bergisch Gladbach; Cornelia Lensch, Wermelskirchen; Michael Immenkeppel, Bonn; Hans-Dieter Block; Herbert Odenbach, both of Leverkusen, all of Fed. Rep. of Germany

[73] Assignee: Bayer Aktiengesellschaft, Leverkusen, Fed. Rep. of Germany

[21] Appl. No.: 394,592

[22] Filed: Aug. 16, 1989

[30] Foreign Application Priority Data

Sep. 3, 1988 [DE] Fed. Rep. of Germany ....... 3829961

[51] Int. Cl.$^5$ ............................. C07F 9/38; C07F 9/40
[52] U.S. Cl. ........................................ 562/24; 558/126
[58] Field of Search ........................................... 562/24

[56]  References Cited

U.S. PATENT DOCUMENTS

| 3,886,204 | 5/1975 | Geffers et al. | 562/24 |
| 3,886,205 | 5/1975 | Geffers et al. | 562/24 |
| 3,923,876 | 12/1975 | Heins et al. | 562/24 |
| 4,020,101 | 4/1977 | Geffers et al. | 562/24 |

FOREIGN PATENT DOCUMENTS 59897  9/1982  European Pat. Off. ............. 562/24

Primary Examiner—J. E. Evans
Attorney, Agent, or Firm—Sprung Horn Kramer & Woods

[57]  ABSTRACT

This invention relates to an improved process for the continuous production of 2-phosphonobutane-1,2,4-tricarboxylic acid (PBTC) and alkali metal salts thereof, in which dialkylphosphite, and ethene-1,2-dicarboxylic acid dialkyl ester, are reacted in the presence of a basic catalyst to form phosphonosuccinic acid tetraalkyl ester, the ester thus obtained is directly reacted with alkyl-acrylate, in the presence of an alkaline catalyst and the reaction product thus obtained is directly hydrolyzed to PBTC or alkali metal salts thereof.

8 Claims, No Drawings

PROCESS FOR THE CONTINUOUS PRODUCTION OF 2-PHOSPHONE-BUTANE-1,2,4-TRICARBOXYLIC ACID AND ALKALI METAL SALTS THEREOF

This invention relates to an improved process for the continuous production of 2-phosphonobutane-1,2,4-tricarboxylic acid (PBTC) and alkali metal salts thereof, in which dialkylphosphite, preferably dimethyl or diethylphosphite, and ethene-1,2-dicarboxylic acid dialkyl ester, particularly the dimethyl or diethyl ester of maleic acid and/or fumaric acid, are reacted in the presence of a basic catalyst to form phosphonosuccinic acid tetraalkyl ester, the ester thus obtained is directly reacted with alkylacrylate preferably methyl or ethylacrylate, in the presence of an alkaline catalyst and the reaction product thus obtained is directly hydrolyzed to PBTC or alkali metal salts thereof.

It had previously been found that phosphonosuccinic acid tetraalkyl esters can be prepared from dialkylphosphite and maleic acid or fumaric acid dialkyl ester in the presence of alkali alcoholates in an addition reaction of the Michael type (A. N. Pudovik, Izv. Akad. Nauk. SSSR Otdel Khim Nauk 1952, pages 821–824). The tetramethyl or tetraethyl esters of phosphonosuccinic acid prepared in this way are purified by distillation and are obtained in a yield of approximately 80%.

DE-OS No. 2 061 838 describes the synthesis of PBTC by reaction of equimolar quantities of phosphonosuccinic acid tetramethyl ester with methylacrylate or acrylonitrile in the presence of 100–150 mmol/mol sodium methanolate as catalyst and subsequent hydrolysis with dilute hydrochloric acid. In this process, distilled phosphonosuccinic acid tetramethyl ester is used and the intermediate product, 2-phosphonobutane-1,2,4-tricarboxylic acid pentamethyl ester or 2-dimethylphosphono-4-nitrilobutane-1,2-dicarboxylic acid dimethyl ester, is freed from volatile secondary products in vacuo at 80° to 90° C. before the hydrolysis step.

Other state-of-the-art processes for the hydrolysis of 2-phosphonobutane-1,2,4-tricarboxylic acid pentamethyl ester, such as hydrolysis in the absence of hydrolysis catalysts foreign to the system (DE-OS No. 2 229 087) and pressure hydrolysis (DE-OS No. 2 745 982), start out from pre-purified educts.

Now, certain disadvantages attending the conventional methods for producing 2-phosphonobutane-1,2,4-tricarboxylic acid are that the phosphonosuccinic acid tetraalkyl ester has to be purified by distillation and, before the hydrolysis of 2-phosphonobutane-1,2,4-tricarboxylic acid pentaalkyl ester, the readily volatile substances have to be distilled off in vacuo at a sump temperature of up to 100° C. to purify the product.

The object of the present invention is to develop a continuous process in which the disadvantages described above are avoided.

The present invention relates to a process for the production of 2-phosphonobutane-1,2,4-tricarboxylic acid or alkali metal salts thereof with complete or partial replacement of the acid protons by alkali metal cations which is characterized in that phosphorous acid dialkyl ester is continuously reacted with ethene-1,2-dicarboxylic acid dialkyl ester, in which the alkyl groups in both reactants independently of one another are methyl or ethyl groups, in a molar ratio of 1:1 to 1:1.1 and preferably in a molar ratio of 1.03 to 1:1.07 in the presence of alkali metal methylate or ethylate to form phosphonosuccinic acid tetraalkyl ester and the reaction product thus obtained is directly reacted without working up or purification by addition of 0.9 to 1.1 mol and preferably 1 to 1.07 mol alkylacrylate, in which the alkyl groups are methyl or ethyl groups, in the presence of alkali metal methylate or ethylate as catalyst and addition of 0.4 to 1.3 mol and preferably about 0.6 mol methanol or ethanol per mol PBTC to be produced as solvent or diluent to form 2-phosphonobutane-1,2,4-tricarboxylic acid pentaalkyl ester, in which the alkyl groups are methyl or ethyl groups, and the reaction product is subjected without further working up to acidic hydrolysis and preferably to PBTC-catalyzed hydrolysis at a temperature in the range from 100° to 150° C. and preferably at a temperature in the range from 105° to 130° C.

The product PBTC thus obtained is surprisingly distinguished by a purity equivalent to that of the product obtained by the conventional process with purification by distillation in the intermediate stages. Surprisingly, secondary products are largely removed together with the alcohol in gaseous form during the hydrolysis with steam. The alcohol or alcohol mixture removed with the steam may be recovered in highly pure form by distillation from the aqueous, alkalized condensate contaminated by steam-volatile substances.

The process according to the invention enables the desired products, PBTC or alkali metal salts thereof, to be obtained in high yields in a technically simple manner without the formation of unwanted secondary products and without having to use excess reactants or auxiliaries requiring subsequent removal. The process according to the invention enables PBTC to be synthesized on an industrial scale more economically in terms of energy by eliminating the hitherto necessary distillation steps between the individual synthesis stages and, hence, more easily by saving the apparatus which would otherwise be necessary for that purpose.

Accordingly, the invention provides a process which enables PBTC and salts thereof, which are now very widely used (for example as scale and corrosion inhibitors in the treatment of cooling water, as incrustation inhibitors in industrial cleaners, as sequestrants and dispersants), to be very easily produced in a highly pure form.

The process according to the invention is illustrated by the following Example.

EXAMPLE 9.52 kg/h maleic acid dimethyl ester (66.11 mol), 5.52 kg/h dimethylphosphite (62.55 mol) and 88 g/h 25% methanolic sodium methylate solution (0.65 mol-%) are introduced as catalyst into the stirred reaction vessel of a continuous plant. The temperature in the reactor I is 40° C. After an average residence time of approximately 220 minutes, the reaction mixture flows into a second reaction vessel.

In the second reactor (reactor II) 5.68 kg/h methyl acrylate (66.05 mol), 244 g/h 25% methanolic sodium methylate solution (1.81 mol-%) and 1.2 kg/h methanol (37.6 mol) are added to the inflow from reactor I. The reaction temperature is 5° C. and the average residence time 220 minutes. The reaction product, which leaves the second reactor through an overflow, has the following composition (gas chromatographic analysis, percentage areas):

17.0% methanol 0.7% methyl acrylate
1.3% methanephosphonic acid dimethyl ester
0.8% methoxysuccinic acid methyl ester
1.9% phosphonosuccinic acid tetramethyl ester
0.4% 2-phosphonopropane-1,2-dicarboxylic acid tetramethyl ester
73.8% 2-phosphonobutane-1,2,4-tricarboxylic acid pentamethyl ester The crude ester flowing off from reactor II is completely hydrolyzed over a period of 12 hours at 100° to 130° C. in a self-catalyzed reaction. 32.8 kg/h of a 50% by weight aqueous solution having the following composition accumulate ($^{31}$PNMR spectrum):

0.2 mol-% phosphoric acid
3.7 mol-% phosphonosuccinic acid
4.3 mol-% phosphonobutane tricarboxylic acid monomethyl ester
87.0 mol-% phosphonobutane tricarboxylic acid
0.7 mol-% phosphonopropionic acid

What is claimed is:

1. A process for the continuous production of 2-phosphonobutane-1,2,4-tricarboxylic acid or alkali metal salts thereof from dialkylphosphite, ethene-1,2-dicarboxylic acid dialkyl ester and alkyl acrylate, comprising preparing phosphonosuccinic acid tetraalkyl ester by reacting dialkylphosphite and ethene-1,2-dicarboxylic acid dialkyl ester in the presence of an alkaline catalyst, at temperatures in the range from 0° to 100° C., reacting the phosphonosuccinic acid tetraalkyl ester thus produced without purification or concentration with alkyl acrylate in the presence of an alkaline catalyst, at temperatures of from −20° to 80° C. to form 2-phosphonobutane-1,2,4-tricarboxylic acid pentaalkyl ester and subjecting the pentaalkyl ester thus produced without intermediate purification or concentration to acidic hydrolysis at a temperature in the range from 100° to 150° C.

2. A process according to claim 1, wherein the alkyl esters are the same or independently of one another are methyl and ethyl ester.

3. A process according to claim 1, wherein the alkaline catalysts are alkali methanolate or alkali ethanolate.

4. A process according to claim 1, wherein the phosphonosuccinic acid tetraalkyl ester is prepared with the addition of a solvent or diluent.

5. A process according to claim 1, wherein the reaction of the phosphonosuccinic acid tetraalkyl ester with alkylacrylate is carried out with the addition of a solvent or diluent.

6. A process according to claim 4, wherein the solvent or diluent is methanol and/or ethanol.

7. A process according to claim 5, wherein the solvent or diluent is methanol and/or ethanol.

8. A process according to claim 1, wherein the acidic hydrolysis is self-catalyzed with no addition of foreign acid.

* * * * *